US007713435B2

(12) United States Patent
Smith et al.

(10) Patent No.: US 7,713,435 B2
(45) Date of Patent: May 11, 2010

(54) HEAT EXCHANGE FLUIDS COMPRISING AMINE CARBOXYLATES

(75) Inventors: Kevin W. Smith, McMurray, PA (US);
Larry W. Gatlin, Floresville, TX (US);
John H. Hallman, New Waverly, TX (US)

(73) Assignee: Clearwater International, L.L.C., Houston, TX (US)

( * ) Notice: Subject to any disclaimer, the term of this patent is extended or adjusted under 35 U.S.C. 154(b) by 0 days.

(21) Appl. No.: 12/273,327

(22) Filed: Nov. 18, 2008

(65) Prior Publication Data

US 2009/0184286 A1 Jul. 23, 2009

Related U.S. Application Data

(62) Division of application No. 11/251,058, filed on Oct. 14, 2005, now Pat. No. 7,452,480, which is a division of application No. 10/141,390, filed on May 8, 2002, now Pat. No. 7,060,198.

(51) Int. Cl.
C09K 5/00 (2006.01)

(52) U.S. Cl. .............................. 252/71; 252/73; 252/74; 252/75; 252/76

(58) Field of Classification Search ........................ None
See application file for complete search history.

(56) References Cited

U.S. PATENT DOCUMENTS

| | | | |
|---|---|---|---|
| 3,742,096 A | 6/1973 | Spivack | |
| 3,901,715 A | 8/1975 | Callahan et al. | |
| 3,950,950 A | 4/1976 | Doerner et al. | |
| 3,952,051 A | 4/1976 | Ogawa et al. | |
| 3,962,874 A | 6/1976 | Doerner | |
| 4,105,592 A | 8/1978 | Collins | |
| 4,117,794 A | 10/1978 | Sjogren | |
| 4,153,473 A | 5/1979 | Rosenberg et al. | |
| 4,192,760 A | 3/1980 | Junger et al. | |
| 4,355,079 A * | 10/1982 | Rosenberg et al. ........... | 428/469 |
| 4,372,932 A | 2/1983 | Hass | |
| 4,444,672 A | 4/1984 | Gancy | |
| 4,537,694 A | 8/1985 | Horodysky | |
| 4,581,039 A | 4/1986 | Horodysky | |
| 4,849,119 A | 7/1989 | Horodysky | |
| 4,954,279 A | 9/1990 | Ma et al. | |
| 5,064,551 A | 11/1991 | Smith | |
| 5,104,562 A | 4/1992 | Kardos et al. | |
| 5,131,233 A | 7/1992 | Cray et al. | |
| 5,334,323 A | 8/1994 | Schrimpf et al. | |
| 5,380,706 A | 1/1995 | Himes et al. | |
| 5,390,505 A | 2/1995 | Smith et al. | |
| 5,398,497 A | 3/1995 | Suppes | |
| 5,435,930 A | 7/1995 | Chan et al. | |
| 5,555,738 A | 9/1996 | DeVault | |
| 5,635,458 A | 6/1997 | Lee et al. | |
| 5,725,637 A | 3/1998 | Gavlin et al. | |
| 5,759,436 A | 6/1998 | Schrimpf et al. | |
| 5,772,912 A | 6/1998 | Lockyer et al. | |
| 5,846,450 A | 12/1998 | Atkinson | |
| 5,853,458 A | 12/1998 | Gavlin et al. | |
| 5,935,488 A | 8/1999 | Wiesenfeld et al. | |
| 5,993,684 A | 11/1999 | Back et al. | |
| 6,058,695 A | 5/2000 | Ranasinghe et al. | |
| 6,059,989 A | 5/2000 | Stankowiak et al. | |
| 6,059,996 A | 5/2000 | Minks et al. | |
| 6,156,226 A | 12/2000 | Klyosov et al. | |
| 6,195,997 B1 | 3/2001 | Lewis et al. | |
| 6,221,276 B1 | 4/2001 | Sarin | |
| 6,239,183 B1 | 5/2001 | Farmer et al. | |
| 6,287,480 B1 | 9/2001 | Berglund et al. | |
| 6,301,897 B1 | 10/2001 | Uchida | |
| 6,321,552 B1 | 11/2001 | Frederiksen | |
| 6,368,384 B1 | 4/2002 | Smith | |
| 6,470,686 B2 | 10/2002 | Pierson | |
| 6,893,582 B2 * | 5/2005 | Smith et al. .................... | 252/76 |
| 7,060,198 B2 | 6/2006 | Smith et al. | |
| 2002/0003223 A1 | 1/2002 | Smith et al. | |

(Continued)

FOREIGN PATENT DOCUMENTS

DE        44 31 233 A1     3/1995

(Continued)

OTHER PUBLICATIONS

Alco Gas & Oil Production Equipment Ltd., "Designed and Manufactured Products Heaters", Internet Article, retrieved from the internet on Mar. 21, 2009, last modified on Dec. 21, 2000.

(Continued)

Primary Examiner—Necholus Ogden, Jr.
(74) Attorney, Agent, or Firm—Patterson & Sheridan LLP

(57) ABSTRACT

Carboxylate salts of amines are used as components of heat exchange fluids. The amines may have a ratio of N to C of 1:0 to 1:12 and the carboxylate anion may be derived from an acid of the formula $H(CH_2)_{0-3}COOH$. A preferred monoamine heat exchange fluid utilizes triethanolamine formate. Lower carboxylate salts of diamines and triamines having the formula $R_2[N[(CH_2)_mNR]_{1-2}]R$ where each R is independently selected from moieties of the formula $—C_nH_{2n+1}$ and moieties of the formula $H[O(CH_2)_{1-4}]—$, each m is independently a number from 1 to 6, and each n is a number from 1 to 4, are disclosed as compounds.

20 Claims, No Drawings

U.S. PATENT DOCUMENTS

2003/0034478 A1* 2/2003 Stanley et al. .................. 252/70

FOREIGN PATENT DOCUMENTS

| DE | 196 04 102 C1 | 7/1997 |
| GB | 606962 A | 8/1948 |
| GB | 716598 A | 10/1954 |
| GB | 903885 A | 8/1962 |
| GB | 1 585 265 A | 2/1981 |
| RU | 1 786 020 A1 | 1/1993 |
| WO | WO-95/29371 A1 | 11/1995 |
| WO | WO-96/39472 A1 | 12/1996 |
| WO | WO-97/01612 A1 | 1/1997 |
| WO | WO-99/37733 A1 | 7/1999 |
| WO | WO-01/81497 A2 | 11/2001 |
| WO | WO-01/94494 A1 | 12/2001 |
| WO | WO-01/96723 A1 | 12/2001 |
| WO | WO-03/012001 A1 | 2/2003 |

OTHER PUBLICATIONS

XP-002249817, Derwent Publiations Ltd., GB; AN 1994-033101, Section Ch, Week 199404 (English translation of the Abstract for foreign patent SU 1786020A1), nma.

Aittomaki A., et al., Potassium Formate As A Secondary Refrigerant, International Journal of Refrigeration, pp. 276-282, vol. 20, No. 4, Jun. 1997.

* cited by examiner

HEAT EXCHANGE FLUIDS COMPRISING AMINE CARBOXYLATES

CROSS-REFERENCE TO RELATED APPLICATIONS

This application is a divisional of U.S. Ser. No. 11/251,058, filed Oct. 14, 2005, now U.S. Pat. No. 7,452,480, which is a divisional of U.S. Ser. No. 10/141,390, filed May 8, 2002, now U.S. Pat. No. 7,060,198, which patent applications are herein incorporated by reference in their entirety.

BACKGROUND OF THE INVENTION

1. Field of the Invention

Aqueous solutions of amine carboxylates, preferably triethanolamine formate, are used as heat exchange fluids.

2. Description of the Related Art

Fluids used for heat exchange in many contexts suffer from the fact that they are either inefficient or environmentally questionable. There is a need for new heat exchange fluids that are environmentally acceptable as well as efficient.

SUMMARY OF THE INVENTION

The present invention comprises the use of solutions of amine carboxylates as heat exchange fluids. Useful compositions combine amines of the formula $R^1R^2R^3N$ with carboxylic acids of the formula $H(CH_2)_{0-2}COOH$, preferably in equimolar ratios, where $R^1$, $R^2$, and $R^3$ are independently selected from moieties of the formula $C_nH_{2n+1}$ and moieties of the formula $H[O(CH_2)_{1-4}]$—, where n is an integer from 0 to 4. Since the compositions will be in aqueous solution, it is useful to express them in the dissolved form. For example, our preferred compound, triethanolamine formate, comprises the reaction product of molar equivalents of triethanolamine and formic acid, and has the formula $(HOCH_2CH_2)_3NH^+HCOO^-$ in water. To make it, the triethanolamine may be added first to water; then formic acid is added slowly to control the exotherm from the neutralization between the acid and the amine. Neutralization is effected preferentially with respect to any possible esterification which could occur between the carboxylic acid and any hydroxyl groups present in the amine. The solution becomes transparent after mixing for a few hours. More generally, where any of several carboxylic acids is used, the formulation in water may be expressed $R_3N^+H(CH_2)_{0-3}COO^-$, where each R is independently as defined above for $R^1$, $R^2$, and $R^3$.

Definition: We use the term "triethanolamine formate" to mean any of (a) a mixture of 1 mole of triethanolamine ("TEA") and one mole of formic acid, (b) a mixture of triethanolamine and formic acid in a molar ratio of 1:4 to 4:1, (c) a composition of the formula $(HOCH_2CH_2)_3NH^+HCOO^-$, or (d) a combination of (a) or (b) with (c) in a ratio up to 100:1. Similar references can be made to such compositions within the above general formula as diethylamine acetate, monoethanolamine propionate, ammonium formate, and trimethylamine formate.

We are not limited to the monoamines described above. Our invention includes the use of diamine carboxylates—for example, compounds of the general formula $R_2NCH_2CH_2NR_2$ where each R is independently selected from moieties of the formula $C_nH_{2n+1}$ and moieties of the formula $H[O(CH_2)_{1-4}]$—, where n is an integer from 0 to 4, are reacted with a carboxylic acid as described above for triethanolamine formate, preferably with the nitrogen and carboxylic groups being present in molar equivalents. Such diamines are included (and are useful in our invention) in the general formula $R_2N(CH_2)_mNR_2$ where each R is defined independently as stated above and m is an integer from 1 to 6. Moreover, we may use any triamine of the formula $R_2N(CH_2)_mNR(CH_2)_mNR_2$, where each R is defined independently as stated above and each m is independently an integer from 1 to 6. In each case—that is, with reference to both diamines and triamines, at least one of the amine nitrogens is associated with a carboxylate group having 1-4 carbon atoms, as described above with reference to the monoamines [that is, $H(CH_2)_{0-3}COO^-$]. Thus, we include such compounds as tetrakishydroxyethylenediamine for association with at least one carboxylate group of formic, acetic or propionic acid. Mixtures of amines useful in our general formulas may be found in such materials as amine heads, the term applied to an unrefined mixture of alkyl diamines having about 4 to 6 carbon atoms, commercially available as a byproduct of the manufacture of hexamethylene diamine and similar products. Such mixtures commonly include various cyclic amines, which are also useful in our invention. Any such mixtures may be reacted with the carboxylic acids described to obtain compositions useful in our invention. As a general principle, we may use any mono-, di-, or triamine, cyclic or not, having an atomic ratio of N to C from 1:0 to 1:12 for combination with the carboxylate of the type described above. A general formula for the amines, including ammonia, the monoamines, diamines and triamines, is $R_2[N[(CH_2)_mNR]_{0-2}]R$, where each R is independently as defined above and each m is independently an integer from 1 to 6. At least one of the nitrogens of such amines is associated with a carboxylate group as explained above. Further, the amine may be additionally ethoxylated, propoxylated, or butoxylated to contain up to three additional alkoxy groups in each R. Examples of compounds within this general formula include ethylene diamine diformate, hexamethylene diamine diformate, hexamethylene diamine diacetate, tetrakis diethoxy hexamethylene diamine diformate, and tetrakis ethanol ethylene diamine dipropionate. An example of a triamine derivative is [HO(CH_2)_2O(CH_2)_2]_2N(CH_2)_2NR(CH_2)_2N[(CH_2)_2O(CH_2)_2OH]_2$, were R is a defined above and in which one, two, or three of the nitrogens is associated with a formate, acetate or propionate group.

We believe certain of the diamine and triamine carboxylates are novel compositions of matter. They may be made in a manner similar to that of the monoamines, i.e., the amine may be added first to water; then the carboxylic acid is added slowly to control the exotherm from the neutralization between the acid and the amine. The solution becomes transparent after mixing for a few hours. Generally, the neutralization reaction takes place in preference to any esterification possible with hydroxyl groups which may be present. Thus our invention includes as new compositions of matter the diamine and triamine carboxylates described herein where the R groups have at least one carbon atom. In each case, a carboxylate group is associated with at least one of the nitrogens of the amine group; preferably each nitrogen has an associated carboxylate group. Stated differently, our invention includes amine carboxylates comprising the neutralization reaction product of an amine of the formula $R_2[N[(CH_2)_mNR]_{1-2}]R$ and an acid of the formula $H(CH_2)_{0-3}COOH$ where each R is independently selected from moieties of the formula —$C_nH_{2n+1}$ and moieties of the formula $H[O(CH_2)_{1-4}]$—, each m is independently a number from 1 to 6, and n is a number from 1 to 4.

Our invention includes the use of the compositions or formulations described above as heat exchange media. The compositions and formulations may replace virtually any commonly or commercially used liquid heat exchange medium, such as a glycol or a mixture of glycols, or an aqueous solution of them, whether used primarily for heating or cooling. Common uses for liquid heat exchange media are in heat pumps, line heaters in gas transmission, thermal energy storage systems, cooling in various molding processes such as blow molding, and any other process or device where it is desired to transfer heat from one place to another. The solutions may be circulated (pumped, for example) to accomplish the heat transfer or it may be conducted or convected in place. When we use the term "heat exchange" we mean to include all such uses, whether or not the liquid is recirculated. Any of the compositions and solutions mentioned herein may also be used in evaporative cooling systems, such as a cooling tower, bearing in mind the desired concentration should be maintained over time. As a practical matter, the heat exchange solution for any of out purposes should include at least 5% by weight of the amine carboxylate, preferably 15 to 80%, and most preferably 25 to 65% by weight, in water, although it should be understood that smaller amounts, say 1% will be effective to a lesser degree but may be useful for some purposes. Often, our heat exchange solutions will be used in enclosed systems having heat exchange surfaces at two locations, and the objective will be to move heat energy from one location (heat exchange surface) to another location (a second heat exchange location), for either heating or cooling purposes at one location or the other and/or to achieve a desired temperature at one location or the other.

When our compositions are used in evaporative systems, i.e. in cooling towers, for example, heat energy is first absorbed into a solution of the composition, which is circulated to a cooling tower or other facility where a portion of the water is evaporated, consuming heat energy from the solution, which is then recirculated, replenished, or both as is known in the art.

Our heat exchange solutions are compatible with potassium formate, and we include combinations of the above described amine carboxylates with potassium formate within our invention. Any solution of the above described amine carboxylates may include potassium formate where the potassium formate is present in amounts up to 10:1 by weight of potassium formate to amine carboxylate, preferably 1:10 to 10:1. In another variant of our invention, where the heat exchange solution comprises at least 5% amine carboxylate of the type defined herein, the alkali metal formate may be present in an amount up to (from 0 or 1%) 50% by weight. Where potassium formate is used, we prefer to use it in weight ratios of the amine carboxylate to potassium formate of 4:1 to 1:4.

DETAILED DESCRIPTION

Certain tests and experiments have been conducted to demonstrate the invention.

First, specific heat determinations were made on three solutions. In the Tables below, the solutions are designated A, B, and C. Solution A is 50% triethanolamine formate in water, Solution B is 80% triethanolamine formate, and Solution C is a combination of 40% triethanolamine formate and 35% potassium formate. Percentages are by weight of the entire composition.

The heated probe technique was used for thermal conductivity (lambda) measurement. Specific heat ($C_p$) values were measured using a differential scanning calorimeter.

In the heated probe method, which may be considered as a variant of the line source method, the line source and temperature sensor are combined in one small diameter probe. This probe is inserted into the sample and the heater turned on for a preselected time interval. During this time interval, the rate of heating of the probe is measured. This heating rate quickly becomes semi-logarithmic and from this semi-logarithmic rate the thermal conductivity of the sample is calculated. The data is collected by a computed-based digital data acquisition system and the heating rate displayed visually. The slope of the temperature curve versus ln time is chosen using cursors and the conductivity calculated is based on this portion of the curve. The method is traceable to ASTM Standard D5334-92.

Specific heat is measured using a standard Perkin-Elmer Model DSC-2 Differential Scanning Calorimeter with sapphire as the reference material. This instrument was calibrated using lead as the standard. The ASTM testing procedure followed was E1269. The standard and sample were subjected to the same heat flux as a blank and the differential powers required to heat the sample and standard at the same rate were determined using the digital data acquisition system. From the masses of the sapphire standard and sample, the differential power, and the known specific heat of sapphire, the specific heat of the sample is computed. The experimental data are visually displayed as the experiment progresses. All measured quantities are directly traceable to NIST standards. Experimental uncertainty of the specific heat measurement is ±4%; experimental uncertainty of the thermal conductivity results are ±7% at room temperature and ±9% at about 70° C. The thermal conductivity results are averages of multiple measurements.

TABLE 1

Specific Heat Results

| Temperature (° C.) | Solution A | Solution B | Solution C |
|---|---|---|---|
| 20 | 3.0020 | 2.4180 | 2.2670 |
| 24 | 3.0330 | 2.4420 | 2.2830 |
| 28 | 3.0650 | 2.4670 | 2.2990 |
| 32 | 3.0950 | 2.4910 | 2.3150 |
| 36 | 3.1230 | 2.5110 | 2.3270 |
| 40 | 3.1520 | 2.5290 | 2.3420 |
| 44 | 3.1690 | 2.5450 | 2.3490 |
| 48 | 3.1890 | 2.5620 | 2.3570 |
| 52 | 3.2090 | 2.5770 | 2.3640 |
| 56 | 3.2310 | 2.5940 | 2.3720 |
| 60 | 3.2540 | 2.6090 | 2.3760 |
| 64 | 3.2780 | 2.6260 | 2.3870 |
| 68 | 3.2980 | 2.6420 | 2.3950 |
| 72 | 3.3220 | 2.6590 | 2.4030 |
| 76 | 3.3420 | 2.6750 | 2.4110 |
| 80 | 3.3630 | 2.6940 | 2.4210 |

TABLE 2

Thermal Conductivity Results

| Sample | Temperature (° C.) | Conductivity (mWcm$^{-1}$K$^{-1}$) |
|---|---|---|
| A | 23.0 | 4.57000 |
|   | 66.0 | 4.72000 |
| B | 23.0 | 3.02000 |
|   | 67.0 | 3.12000 |
| C | 23.0 | 3.55000 |
|   | 73.0 | 3.81000 |

Persons skilled in the art will recognize that the properties of the compositions studied are such that they will make excellent heat exchange materials. Our invention therefore includes a method of transferring heat energy from a first location to a second location comprising absorbing heat energy at the first location into an aqueous solution comprising an amine carboxylate, the amine portion of the amine carboxylate having an atomic ratio of N to C from 1:0 to 1:12 and the carboxylate portion being derived from an acid of the formula $H(CH_2)_{0-3}COOH$, and desorbing the heat energy from the amine carboxylate solution at the second location. The transfer of heat energy may be for cooling or heating, may be effected by convection or conduction, and the removal of heat energy may be accomplished through a heat transfer surface or by evaporation. The absorption of heat energy may also be through a heat transfer surface. Monoamines of the formula $R_3N$, diamines of the formula $R_2N(CH_2)_mNR_2$, and triamines of the formula $R_2[N[(CH_2)_mNR]_2]R$, where each R is independently selected from moieties of the formula $C_nH_{2n+1}$ and moieties of the formula $H[O(CH_2)_{1-4}]—$, where n is an integer from 0 to 4, may be combined with a carboxylic moiety of the formula derived from carboxylic acids having from 1 to 4 carbon atoms, with at least one carboxylate group for each diamine or triamine moiety, but preferably in molar ratios of carboxylate to N of 1. As indicated above, one or more of the $H[O(CH_2)_{1-4}]—$ groups in any of our amine components may be further alkoxylated using alkoxy groups of 1-4 carbon atoms, thus extending a small chain of alkoxy groups on one or more R's.

In one embodiment, an amine carboxylate comprises the reaction product of an amine of the formula $R_2[N[(CH_2)_mNR]_{1-2}]R$ and an acid of the formula $H(CH_2)_{0-3}COOH$ where each R is independently selected from moieties of the formula $—C_nH_{2n+1}$ and moieties of the formula $H[O(CH_2)_{1-4}]—$, each m is independently a number from 1 to 6, and each n is a number from 1 to 4.

In one or more embodiments described herein, the amine carboxylate is in an aqueous solution.

In one or more embodiments described herein, the amine is further alkoxylated.

In one or more embodiments described herein, the amine is a diamine and at least one R is a moiety of the formula $H[O(CH_2)_{1-4}]—$.

In one or more embodiments described herein, the amine carboxylate comprises a formate of a diamine of the formula $R_2N(CH_2)_2NR_2$.

In one or more embodiments described herein, the amine carboxylate comprises a formate of an amine of the formula $R_2N(CH_2)_6NR_2$.

In one or more embodiments described herein, the amine is a diamine and at least one R is a moiety of the formula $—C_nH_{2n+1}$.

In one or more embodiments described herein, the amine is a triamine and at least one R is a moiety of the formula $H[O(CH_2)_{1-4}]—$.

In one or more embodiments described herein, the amine carboxylate being a formate of a triamine of the formula $R_2N(CH_2)_6NR(CH_2)_6NR_2$.

In one or more embodiments described herein, the amine carboxylate being a formate of a triamine of the formula $R_2N(CH_2)_2NR(CH_2)_2NR_2$.

In one or more embodiments described herein, the amine is a triamine and at least one R is a moiety of the formula $—C_nH_{2n+1}$.

In one or more embodiments described herein, the amine carboxylate forms a composition with an alkali metal formate.

In one or more embodiments described herein, the amine carboxylate forms a composition with potassium formate in a weight ratio of 4:1 to 1:4.

In one or more embodiments described herein, the alkali metal formate is in a ratio of alkali metal formate to amine carboxylate of 1:10 to 10:1.

In one or more embodiments described herein, the amine carboxylate comprises a formate of a diamine of the formula $R_2N(CH_2)_2NR_2$.

In one or more embodiments described herein, the amine carboxylate comprises a formate of an amine of the formula $R_2N(CH_2)_6NR_2$.

While the foregoing is directed to embodiments of the present invention, other and further embodiments of the invention may be devised without departing from the basic scope thereof, and the scope thereof is determined by the claims that follow.

The invention claimed is:

1. An amine carboxylate aqueous fluid, comprising:
    a reaction product of an amine of the formula $R_2[N[(CH_2)_mNR]_{1-2}]R$ and an acid of the formula $H(CH_2)_{0-3}COOH$ where each R is independently selected from moieties of the formula $—C_nH_{2n+1}$ and moieties of the formula $H[O(CH_2)_{1-4}]—$, each m is independently an integer from 1 to 6, and each n is an integer from 1 to 4; and
    an alkali metal formate.

2. The amine carboxylate aqueous fluid of claim 1, wherein the amine is further alkoxylated.

3. The amine carboxylate aqueous fluid of claim 1, wherein the amine is a diamine and at least one R is a moiety of the formula $H[O(CH_2)_{1-4}]—$.

4. The amine carboxylate aqueous fluid of claim 1, wherein the amine is a diamine of the formula $R_2N(CH_2)_2NR_2$.

5. The amine carboxylate aqueous fluid of claim 1, wherein the amine is a diamine and at least one R is a moiety of the formula $—C_nH_{2n+1}$.

6. The amine carboxylate aqueous fluid of claim 1, wherein the amine is a triamine and at least one R is a moiety of the formula $H[O(CH_2)_{1-4}]—$.

7. The amine carboxylate aqueous fluid of claim 6, the triamine has the formula $R_2N(CH_2)_6NR(CH_2)_6NR_2$.

8. The amine carboxylate aqueous fluid of claim 1, wherein the amine is a triamine and at least one R is a moiety of the formula $—C_nH_{2n+1}$.

9. The amine carboxylate aqueous fluid of claim 1, wherein the reaction product is triamine formate.

10. The amine carboxylate aqueous fluid of claim 1, wherein the alkali metal formate is potassium formate.

11. The amine carboxylate aqueous fluid of claim 1, wherein a ratio of the alkali metal formate to the reaction product is 1:10 to 10:1.

12. An amine carboxylate aqueous fluid, comprising:
    a reaction product of an amine of the formula $R_2[N[(CH_2)_mNR]]R$ and an acid of the formula $H(CH_2)_{0-3}COOH$ where each R is independently selected from moieties of the formula $—C_nH_{2n+1}$ and moieties of the formula $H[O(CH_2)_{1-4}]—$, each m is independently an integer from 1 to 6, and each n is an integer from 1 to 4; and
    potassium formate.

13. The amine carboxylate aqueous fluid of claim 12, wherein the amine is a diamine and at least one R is a moiety of the formula $H[O(CH_2)_{1-4}]—$.

14. The amine carboxylate aqueous fluid of claim 12, wherein the amine is a diamine of the formula $R_2N(CH_2)_2NR_2$.

15. The amine carboxylate aqueous fluid of claim 12, wherein the amine is a diamine and at least one R is a moiety of the formula $—C_nH_{2n+1}$.

16. The amine carboxylate aqueous fluid of claim 12, wherein a ratio of the potassium formate to the reaction product is 1:10 to 10:1.

17. An amine carboxylate aqueous fluid, comprising:
- a reaction product of an amine of the formula $R_2[N[(CH_2)_mNR]_2]R$ and an acid of the formula $H(CH_2)_{0-3}COOH$ where each R is independently selected from moieties of the formula $-C_nH_{2n+1}$ and moieties of the formula $H[O(CH_2)_{1-4}]-$, each m is independently an integer from 1 to 6, and each n is an integer from 1 to 4; and
- potassium formate.

18. The amine carboxylate aqueous fluid of claim 17, wherein the amine is a triamine and at least one R is a moiety of the formula $H[O(CH_2)_{1-4}]-$.

19. The amine carboxylate aqueous fluid of claim 17, wherein the amine is a triamine of the formula $R_2N(CH_2)_6NR(CH_2)_6NR_2$.

20. The amine carboxylate aqueous fluid of claim 17, wherein the amine is a triamine and at least one R is a moiety of the formula $-C_nH_{2n+1}$.

* * * * *